United States Patent
Maeda

(10) Patent No.: US 8,339,568 B2
(45) Date of Patent: Dec. 25, 2012

(54) FOREIGN PARTICLE INSPECTION APPARATUS, EXPOSURE APPARATUS, AND METHOD OF MANUFACTURING DEVICE

(75) Inventor: Kohei Maeda, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 669 days.

(21) Appl. No.: 12/424,468

(22) Filed: Apr. 15, 2009

(65) Prior Publication Data

US 2009/0263750 A1   Oct. 22, 2009

(30) Foreign Application Priority Data

Apr. 17, 2008 (JP) ................... 2008-108291

(51) Int. Cl.
- *G03B 27/52* (2006.01)
- *G03B 27/42* (2006.01)
- *G03B 27/54* (2006.01)
- *G03B 27/32* (2006.01)

(52) U.S. Cl. .............. 355/30; 355/53; 355/67; 355/77

(58) Field of Classification Search .............. 355/30, 355/53, 67–71, 72, 75, 77; 356/239.7, 239.8, 356/335, 336, 337, 338, 340–343, 237.3–237.5, 356/237.7; 430/5, 8, 22, 30, 322
See application file for complete search history.

(56) References Cited

U.S. PATENT DOCUMENTS

| | | | | |
|---|---|---|---|---|
| 4,966,457 A | * | 10/1990 | Hayano et al. | 356/239.7 |
| 5,229,839 A | * | 7/1993 | Hayashi et al. | 356/336 |
| 5,486,919 A | * | 1/1996 | Tsuji et al. | 356/484 |
| 5,581,348 A | | 12/1996 | Miura et al. | |
| 5,585,916 A | * | 12/1996 | Miura et al. | 356/237.4 |
| 5,936,726 A | * | 8/1999 | Takeda et al. | 356/237.2 |
| 6,091,493 A | * | 7/2000 | Stover et al. | 356/336 |
| 6,138,083 A | * | 10/2000 | Videen | 702/155 |
| 6,169,601 B1 | * | 1/2001 | Eremin et al. | 356/239.8 |
| 6,538,730 B2 | * | 3/2003 | Vaez-Iravani et al. | 356/237.2 |
| 2002/0036771 A1 | * | 3/2002 | Sato et al. | 356/237.4 |
| 2006/0001877 A1 | * | 1/2006 | Moriya | 356/369 |
| 2006/0072108 A1 | * | 4/2006 | Onvlee et al. | 356/239.8 |

FOREIGN PATENT DOCUMENTS

| | | |
|---|---|---|
| JP | 7-005115 A | 1/1995 |
| JP | 7-043312 A | 2/1995 |
| JP | 09-159576 A | 6/1997 |
| JP | 09-304289 A | 11/1997 |
| JP | 11-271231 A | 10/1999 |

* cited by examiner

*Primary Examiner* — Toan Ton
*Assistant Examiner* — Christina Riddle
(74) *Attorney, Agent, or Firm* — Canon USA, Inc., IP Division

(57) ABSTRACT

A foreign particle inspection apparatus includes a light projecting unit, a photo-receiving unit which receives the scattered light, and a controller. The photo-receiving unit is arranged such that its optical axis is tilted by a first angle with respect to a plane including the optical axis and the normal axis to the surface. When the angle of the polarization axis of the projected light with respect to the plane is defined as a second angle, the controller controls at least one of the polarization axis and the arrangement of the photo-receiving unit so that the differences between the first angle and the second angle become a first state and a second state, thereby determining a foreign particle based on the outputs from the photo-receiving unit in the first state and the second state.

11 Claims, 16 Drawing Sheets

FIG. 3
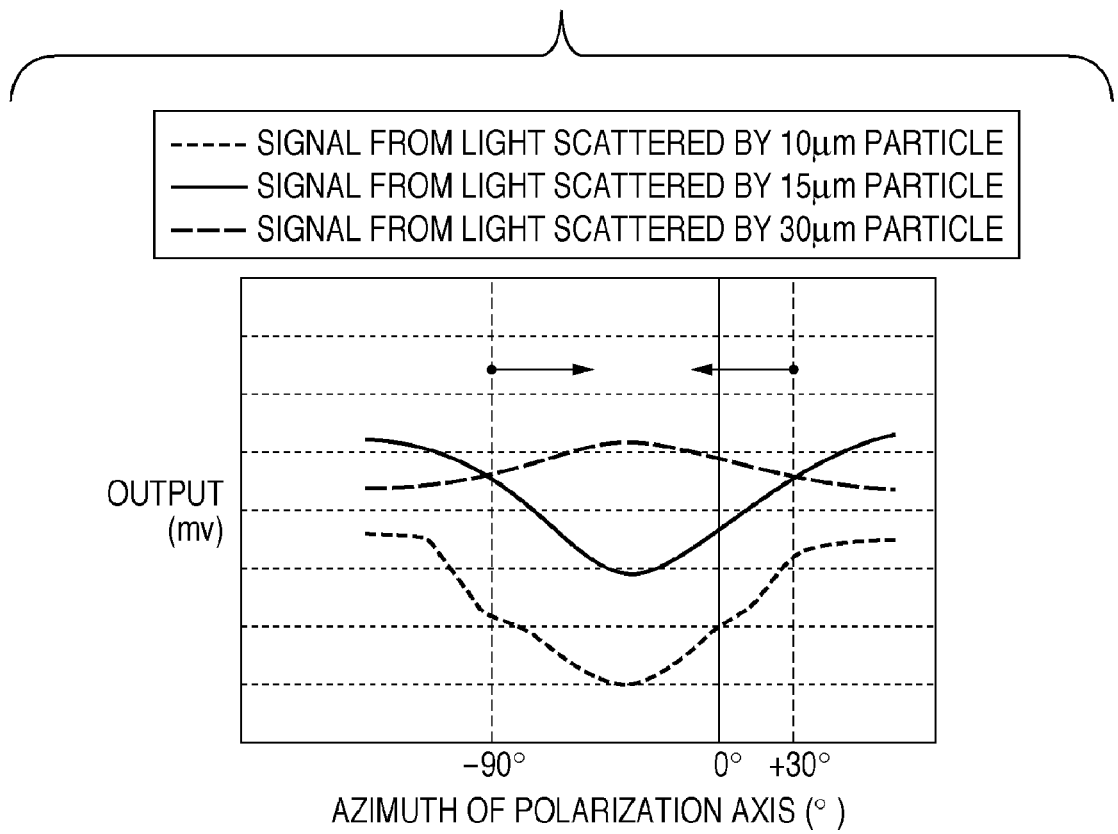
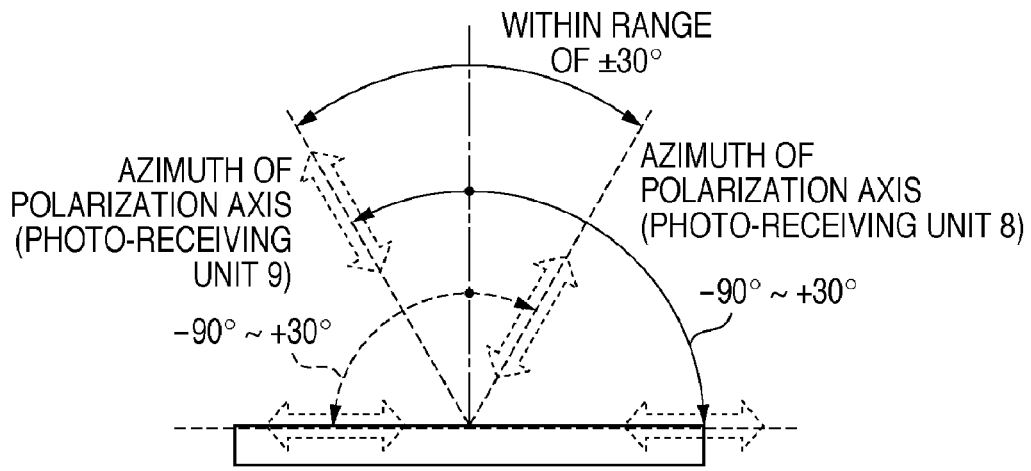

FIG. 4
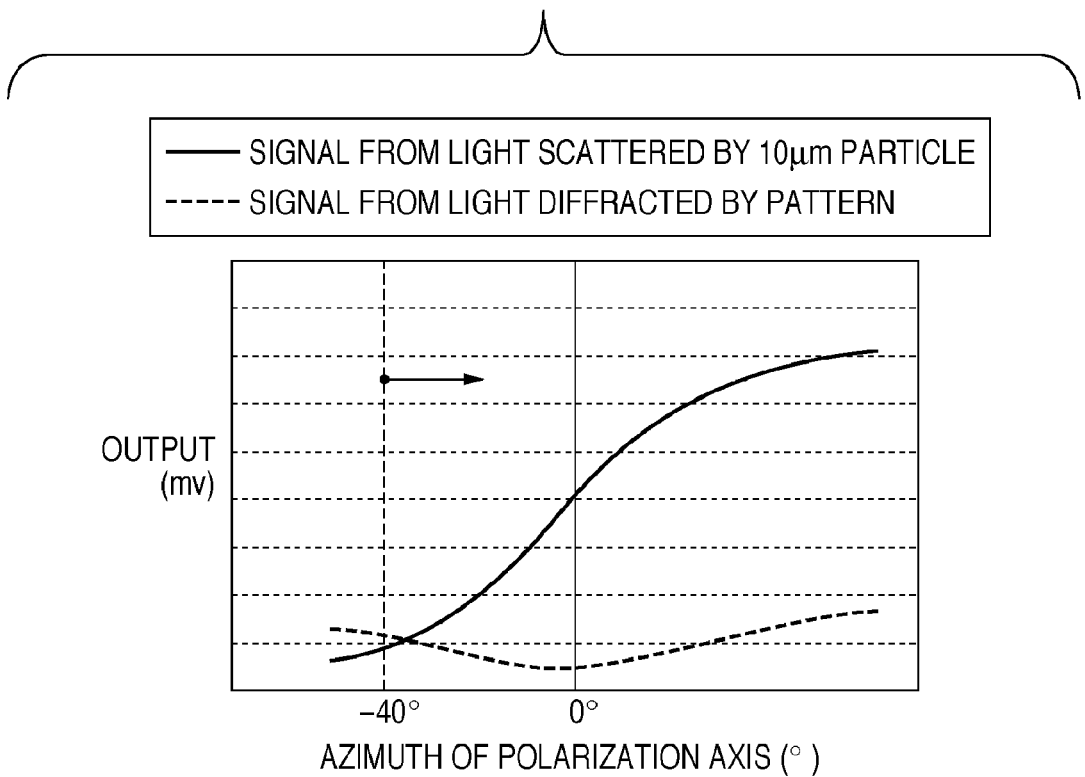
- SIGNAL FROM LIGHT SCATTERED BY 10μm PARTICLE
- - - - SIGNAL FROM LIGHT DIFFRACTED BY PATTERN
OUTPUT (mv)
AZIMUTH OF POLARIZATION AXIS (°)
AZIMUTH α OF POLARIZATION AXIS, AT WHICH OUTPUT OF LIGHT SCATTERED BY 10μm PARTICLE > OUTPUT OF LIGHT DIFFRACTED BY PATTERN, FALLS WITHIN RANGE OF ±40° FOR φ1=−30° AND φ2=+30°
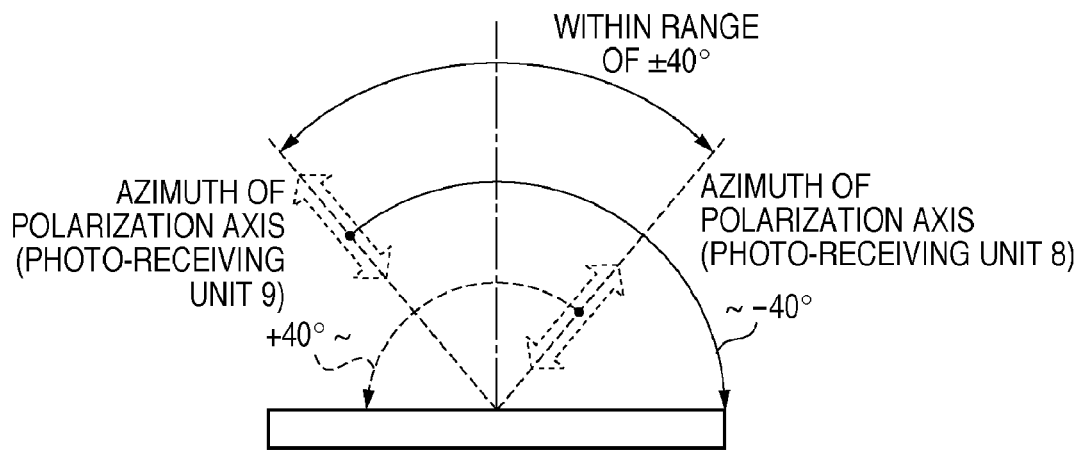

FIG. 5A

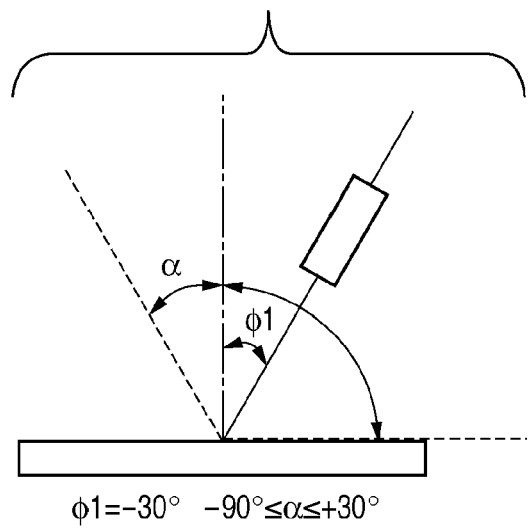

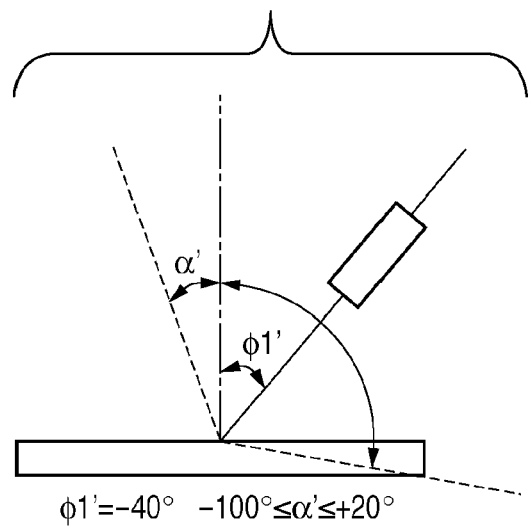

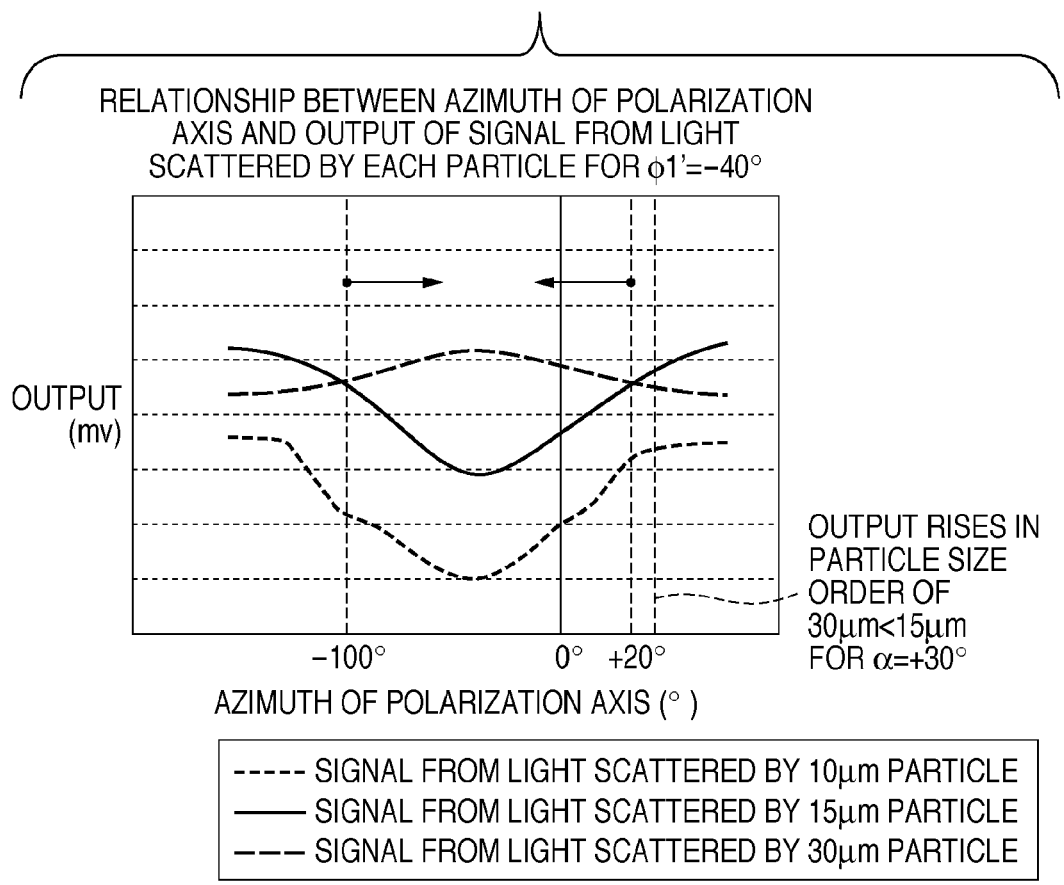

RELATIONSHIP BETWEEN AZIMUTH OF POLARIZATION AXIS AND OUTPUT OF SIGNAL FROM LIGHT SCATTERED BY EACH PARTICLE FOR φ1'=−40°

OUTPUT RISES IN PARTICLE SIZE ORDER OF 30μm<15μm FOR α=+30°

AZIMUTH OF POLARIZATION AXIS (°)

----- SIGNAL FROM LIGHT SCATTERED BY 10μm PARTICLE
—— SIGNAL FROM LIGHT SCATTERED BY 15μm PARTICLE
— — SIGNAL FROM LIGHT SCATTERED BY 30μm PARTICLE

FIG. 7
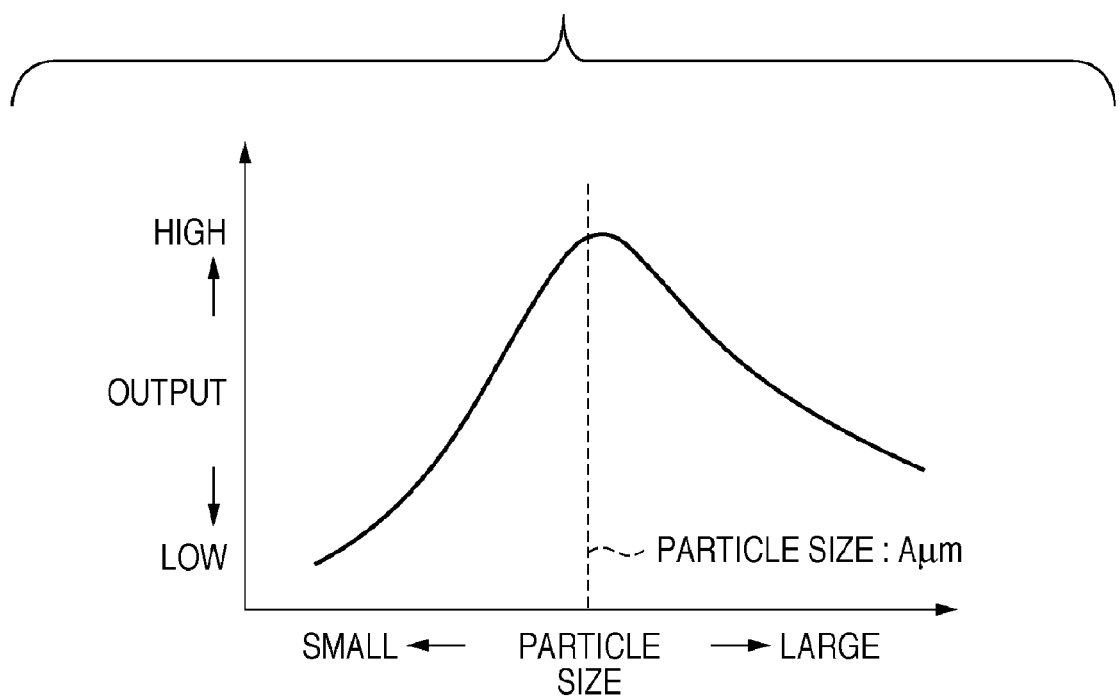
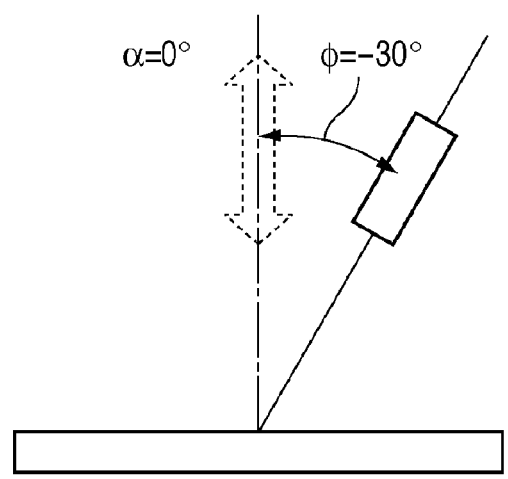

FIG. 8
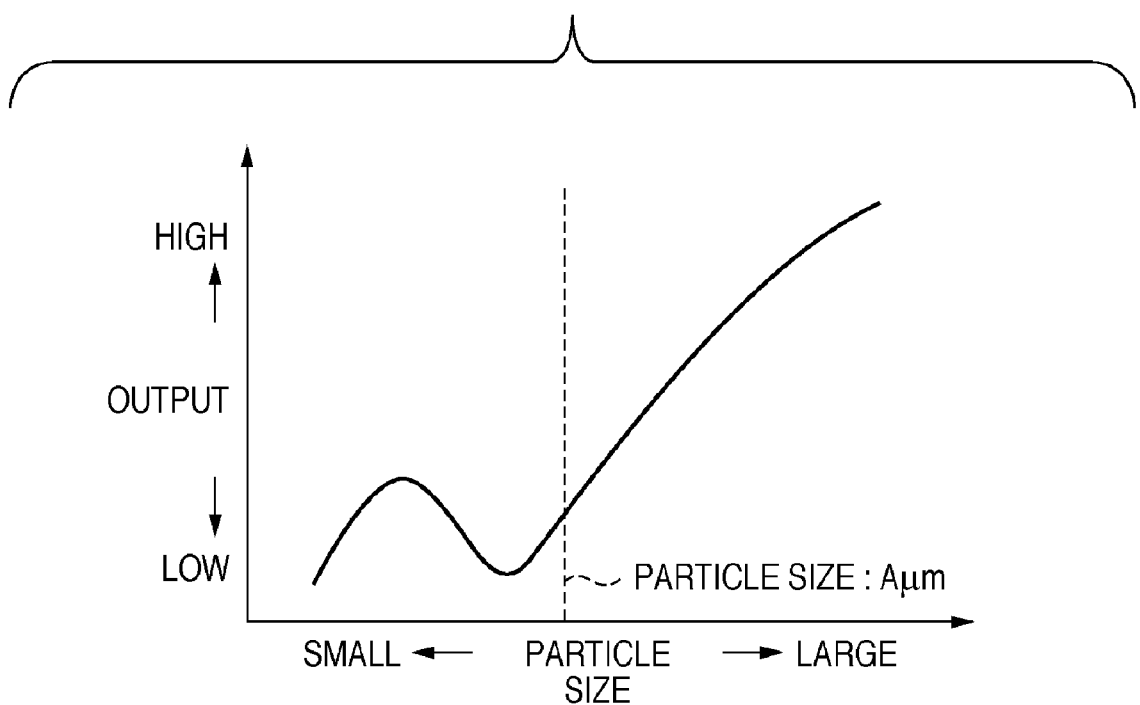
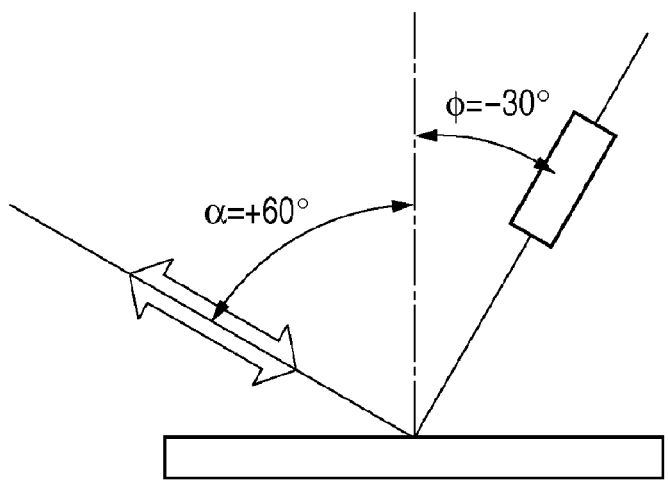

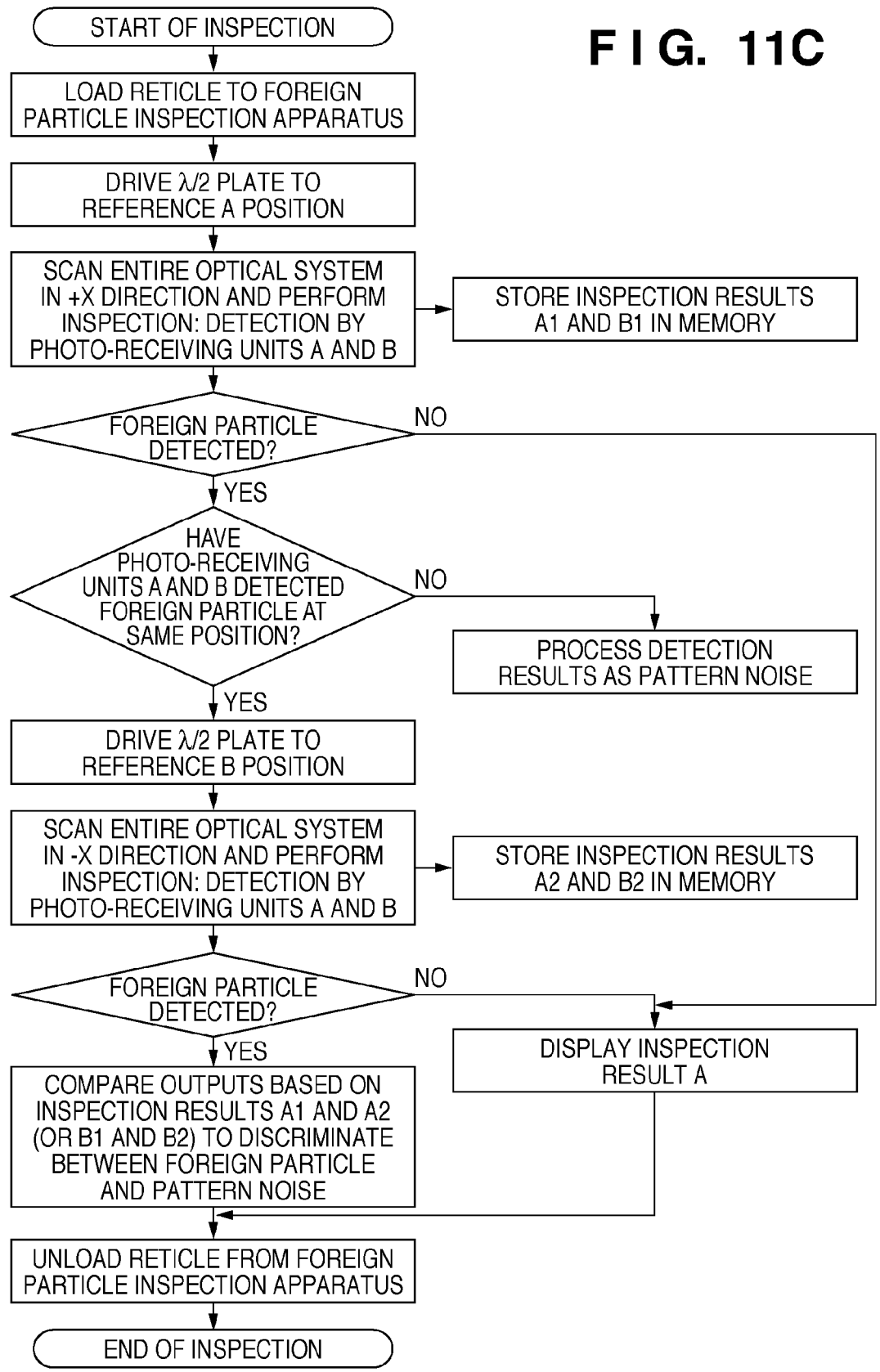
F I G. 11C

FOREIGN PARTICLE INSPECTION APPARATUS, EXPOSURE APPARATUS, AND METHOD OF MANUFACTURING DEVICE

BACKGROUND OF THE INVENTION

1. Field of the Invention

The present invention relates to a foreign particle inspection apparatus, an exposure apparatus, and a method of manufacturing a device.

2. Description of the Related Art

In a process of manufacturing an IC and an LSI, an exposure apparatus transfers a circuit pattern formed on a reticle onto a wafer coated with a resist.

During this transfer, if a pattern defect or a foreign particle or foreign substance such as dust is present on the reticle, it is transferred onto the wafer together with the targeted pattern, resulting in a decrease in the manufacturing yield. Especially when a circuit pattern is repeatedly transferred to a large number of shot regions on the wafer by exposure using the step & repeat scheme, if one harmful foreign particle is present on the reticle, it is also transferred onto the entire wafer surface by exposure. This results in a large decrease in the yield.

For this reason, it is essential to detect the presence of foreign particles on the reticle. To meet this need, a foreign particle inspection apparatus which exploits a property that foreign particles isotropically scatter light is generally used.

For example, a collimated light beam is obliquely projected onto the surface of an object to be inspected from above, and light scattered by a foreign particle is guided onto a one-dimensional image sensor (sensor array) by a gradient-index microlens array, thereby inspecting the surface of the object to be inspected (see Japanese Patent Laid-Open Nos. 7-043312 and 7-005115).

FIGS. 10A and 10B are views showing the basic arrangement of an optical system in a foreign particle inspection apparatus disclosed in Japanese Patent Laid-Open Nos. 7-043312 and 7-005115. For the sake of descriptive convenience, only an optical system for inspecting the blank surface of a reticle for foreign particles will be described herein. In practice, this apparatus also includes an optical system for inspecting, for foreign particles, a pellicle film which protects the circuit pattern surface of the reticle from foreign particles. Referring to FIGS. 10A and 10B, reference numeral 2 denotes a pellicle frame having a pellicle film attached on it.

A laser beam which is emitted by a semiconductor laser 41 and has a certain angle of divergence is collimated into a collimated light beam by a collimator lens 42. A $\lambda/2$ plate 43 guides the laser beam so that the polarization axis of the projected light is parallel to a plane including the optical axis of the projected light and that of the light received by a photo-receiving unit 7. The laser beam strikes the surface of an object to be inspected at an incident angle θ close to 90°. With this operation, the laser beam forms a linear light projection region 5 on a blank surface 1a as the surface of the object to be inspected.

If a foreign particle 3 is present in the light projection region 5, scattered light is generated by the foreign particle 3. This scattered light is converged on a line sensor 72 by an imaging lens 71 (lens array) which is formed by arraying lenses along the longitudinal direction of the light projection region 5 and serves to receive scattered light. The imaging lens 71 is configured to form an image of the light projection region 5 on the line sensor 72. The entire blank surface 1a is inspected for foreign particles by scanning an entire optical system 10 in a direction which is perpendicular to the longitudinal direction of the light projection region 5 and parallel to the blank surface 1a, i.e., by linearly scanning it in the X direction, as shown in FIG. 10B.

To increase the intensity of scattered light in proportion to increases in the particle size, the conventional foreign particle inspection apparatus sets the polarization axis of the laser beam in a direction nearly parallel to a plane including the optical axes of the projected light and the received light.

However, the minimum allowable particle size on the reticle or the pellicle in the recent exposure apparatuses is as small as about 10 µm. For this reason, it is becoming difficult to discriminate between a signal from light scattered by a 10-µm particle on an object to be inspected and that of light diffracted by the circuit pattern of the reticle when the foreign particle inspection apparatus inspects the object to be inspected. Note that the foreign particle inspection apparatus is set such that the intensity of scattered light increases in proportion to increases in the particle size, and that the discrimination performance between a signal from light scattered by a particle on the object to be inspected and that of light diffracted by the pattern improves. To attain this state, the $\lambda/2$ plate 43 included in a light projecting unit 4 (a unit which forms inspection light) optimally sets the azimuth of the polarization axis of the laser beam and that of the optical axis of the photo-receiving unit 7.

A phenomenon in which light diffracted by the pattern on the reticle is falsely detected as scattered light will be described next. FIG. 12 is a view when an optical path along which false detection often occurs is viewed from above the reticle and from the lateral side of a reticle side surface 1c (from the X direction). The light projecting unit 4 irradiates the linear light projection region 5 on the blank surface with a laser beam. Because the incident angle on the blank surface is relatively large, most (90% or more) of the light is reflected, but a certain component of the light enters the reticle. At this time, as the light is refracted at a position P on the blank surface and irradiates a linear circuit pattern 102 extending in the Y direction, pattern-diffracted light 103L and pattern-diffracted light 103R are generated by the circuit pattern 102.

When the circuit pattern 102 is obliquely irradiated with the light, diffracted light scatters in a direction perpendicular to the circuit pattern 102 with reference to light regularly reflected by the circuit pattern 102. Light which enters the reticle at the position P upon striking the reticle at an incident angle close to 90° and being refracted at that position serves as pattern irradiation light. If the light is further diffracted by the pattern, the diffracted light is totally reflected by the blank surface even upon reaching it. Likewise, when the light totally reflected by the blank surface reaches the pattern surface, it is totally reflected in the incident region on the pattern surface again if the circuit pattern is absent in this region. In addition, depending on the density of the circuit pattern 102, the light is often totally reflected by a back side surface 1b of the reticle and the reticle side surface 1c. In this manner, unless the circuit pattern 102 is illuminated again to cause a diffraction phenomenon, the pattern-diffracted light 103L is often totally reflected by all of the pattern surface (irrespective of a light-shielding film portion, a glass portion, or a semitransparent film portion), the blank surface, and the reticle side surfaces.

Also referring to FIG. 12, if the pattern-diffracted light 103L repeatedly undergoes total reflection, it often returns to a position below (in the Z direction) the light projection region 5. If a linear pattern 104 extending in the X direction is present at this position, diffracted light 105 is often generated by it again and received by the photo-receiving unit 7. This phenomenon will be explained with reference to FIG. 13.

FIG. 13 is a view when the optical system shown in FIG. 10A is viewed from the side of the light projecting unit 4. Of the optical path along which the pattern-diffracted light 103L which repeatedly undergoes total reflection travels, that from the reticle side surface 1c to the pattern 104 is indicated by a dotted line. The pattern 104 is a linear pattern in the X direction, so the diffracted light 105 corresponds to that obtained by changing the tilt about the X-axis, which is perpendicular to the pattern 104, with reference to regularly reflected light. For this reason, the diffracted light 105 appears as if it overlapped regularly reflected light in FIG. 13, but FIG. 12 reveals that its incident angle on the blank surface is often smaller than a critical angle and therefore the light emerges into the air. Furthermore, depending on the density of the linear pattern 104, the diffracted light 105 is often diffracted at an angle nearly matching the direction of the optical axis of the imaging lens 71 of the photo-receiving unit, and detected as light scattered by a foreign particle by the line sensor 72.

The pattern-diffracted light 103R repeatedly undergoes total reflection as well, but it is gradually attenuated upon entering a circuit pattern region 101 on the side surface 1b because diffracted light is generated. The generated diffracted light never enters the photo-receiving unit 7, so it is never detected falsely.

SUMMARY OF THE INVENTION

The present invention is directed to a foreign particle inspection apparatus which can precisely inspect an object to be inspected for foreign particles by preventing any false detection due to light diffracted by the pattern.

According to the first aspect of the present invention, there is provided a foreign particle inspection apparatus including a light projecting unit which projects light to a surface of an object to be inspected, a photo-receiving unit which receives the light that is projected to the surface by the light projecting unit and scattered by the surface, and a controller which determines at least one of presence/absence and a size of a foreign particle on the surface based on the output from the photo-receiving unit, wherein the light projecting unit is arranged such that an optical axis of the light projecting unit is tilted with respect to the surface, the photo-receiving unit is arranged such that an optical axis of the photo-receiving unit is tilted by a first angle with respect to a plane including the optical axis of the light projecting unit and a normal axis to the surface, and when an angle of a polarization axis of the projected light with respect to the plane is defined as a second angle, the controller controls at least one of the polarization axis of the projected light and the arrangement of the photo-receiving unit so that differences between the first angle and the second angle become a first state and a second state which are different from each other, thereby determining a foreign particle based on the output from the photo-receiving unit in the first state and the output from the photo-receiving unit in the second state.

According to the present invention, it is possible to provide a foreign particle inspection apparatus which can precisely inspect an object to be inspected for foreign particles by preventing any false detection due to light diffracted by the pattern.

Further features of the present invention will become apparent from the following description of exemplary embodiments with reference to the attached drawings.

BRIEF DESCRIPTION OF THE DRAWINGS

FIG. 3 shows a graph and a diagram of the relationship between the azimuth of the polarization axis and the output of light scattered by a particle;

FIG. 4 shows a graph and a diagram of the relationship between the azimuth of the polarization axis and the output of light scattered by a particle;

FIGS. 5A to 5C are a graph and diagrams showing the relationship between the azimuth of the polarization axis and the output of light scattered by a particle;

FIG. 7 shows a graph and a diagram of the relationship between the particle size and the output of scattered light for $\phi = -30°$ and $\alpha = 0°$;

FIG. 8 shows a graph and a diagram of the relationship between the particle size and the output of scattered light for $\phi = -30°$ and $\alpha = +60°$;

FIG. 11C is a flowchart illustrating still another example of the inspection sequence;

DESCRIPTION OF THE EMBODIMENTS

Embodiments of the present invention will be described in detail below with reference to the accompanying drawings. The embodiments to be described hereinafter are merely examples of the present invention, and can be appropriately modified or changed in accordance with various conditions and the arrangement of an apparatus to which the present invention is applied.

[First Embodiment]

Figure 1A:
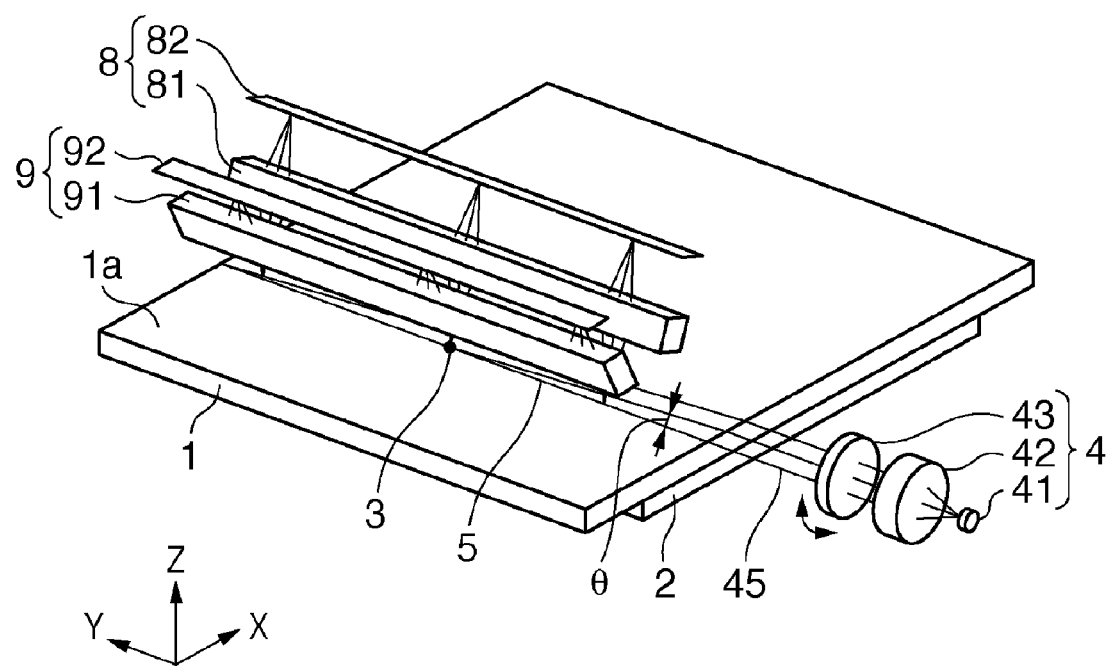
FIGS. 1A and 1B are schematic views showing a foreign particle inspection apparatus according to the first embodiment.
Figure 1B:
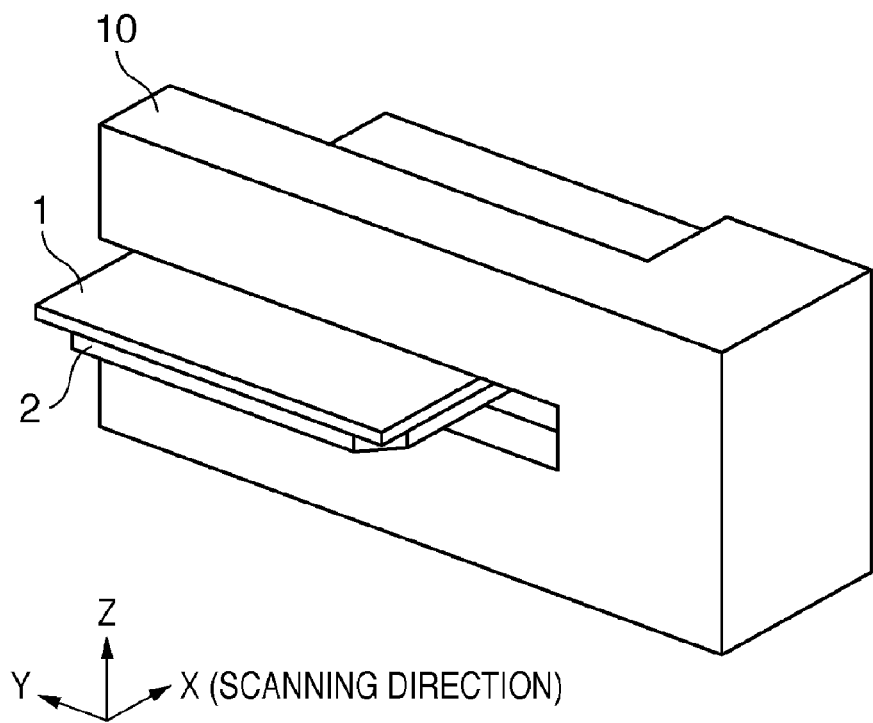

FIGS. 1A and 1B are views showing the basic arrangement of an optical system in a foreign particle inspection apparatus according to the first embodiment. For the sake of descriptive convenience, only an optical system for inspecting a blank surface 1a of a reticle 1 for foreign particles will be described herein. In practice, this apparatus can also include an optical system for inspecting, for foreign particles, a pellicle film which protects the circuit pattern surface of the reticle 1 from foreign particles. Referring to FIGS. 1A and 1B, reference numeral 2 denotes a pellicle frame having a pellicle film attached on it. Accordingly, the object to be inspected can be at least one of the reticle 1 and the pellicle film.

Figure 10A:
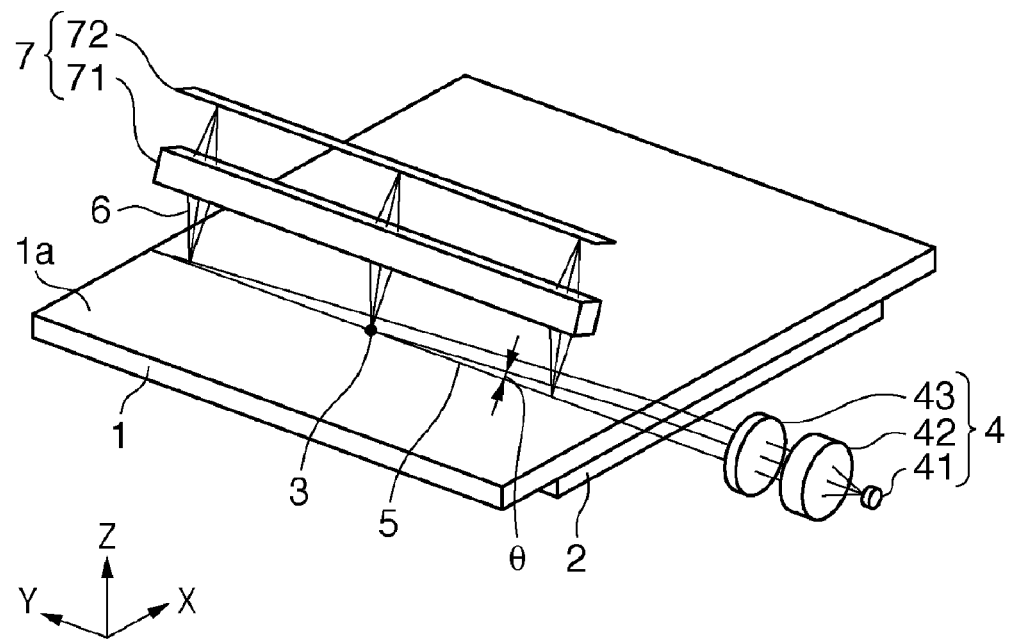
FIGS. 10A and 10B are schematic views showing the conventional foreign particle inspection apparatus.
Figure 10B:
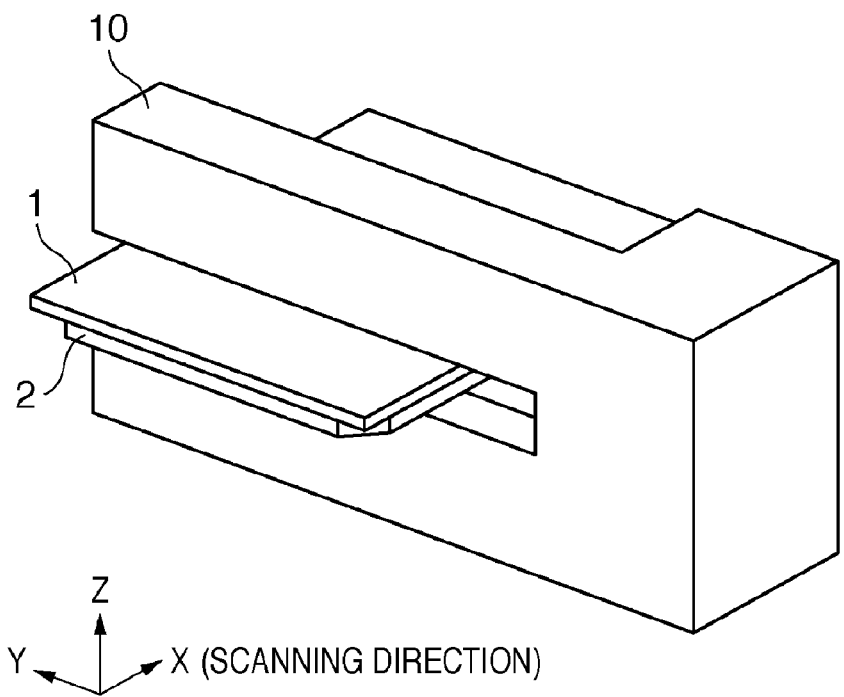

A light projecting unit 4 which projects light to the surface of the reticle 1 includes a semiconductor laser 41, collimator lens 42, and $\lambda/2$ plate 43, as in that shown in FIGS. 10A and 10B. Note that the light projecting unit 4 shown in FIGS. 1A and 1B is provided with a mechanism which can rotationally drive the λ/2 plate 43 about the optical axis. A polarizing filter, λ/4 plate, polarizing element, or the like may be used in place of the λ/2 plate 43. The arrangement of a photo-receiving unit 8 which receives the light that is projected by the light projecting unit 4 and scattered by the blank surface 1a is the same as that of the photo-receiving unit 7 shown in FIG. 10A. However, the foreign particle inspection apparatus shown in FIG. 1A further includes a photo-receiving unit 9 having the same arrangement as that of the photo-receiving unit 8, and a controller (not shown) which determines at least one of the presence/absence and size of a foreign particle on the blank surface 1a based on the outputs from the photo-receiving units 8 and 9. The foreign particle inspection apparatus inspects the entire blank surface 1a for foreign particles by scanning an entire optical system 10 in a direction which is perpendicular to the longitudinal direction of a light projection region 5 and parallel to the blank surface 1a, i.e., by linearly scanning it in the X direction, as shown in FIG. 1B.

The light projecting unit 4 is arranged such that the optical axis of light projected by the light projecting unit 4 is tilted by an angle θ with respect to the blank surface 1a.

Figure 2:
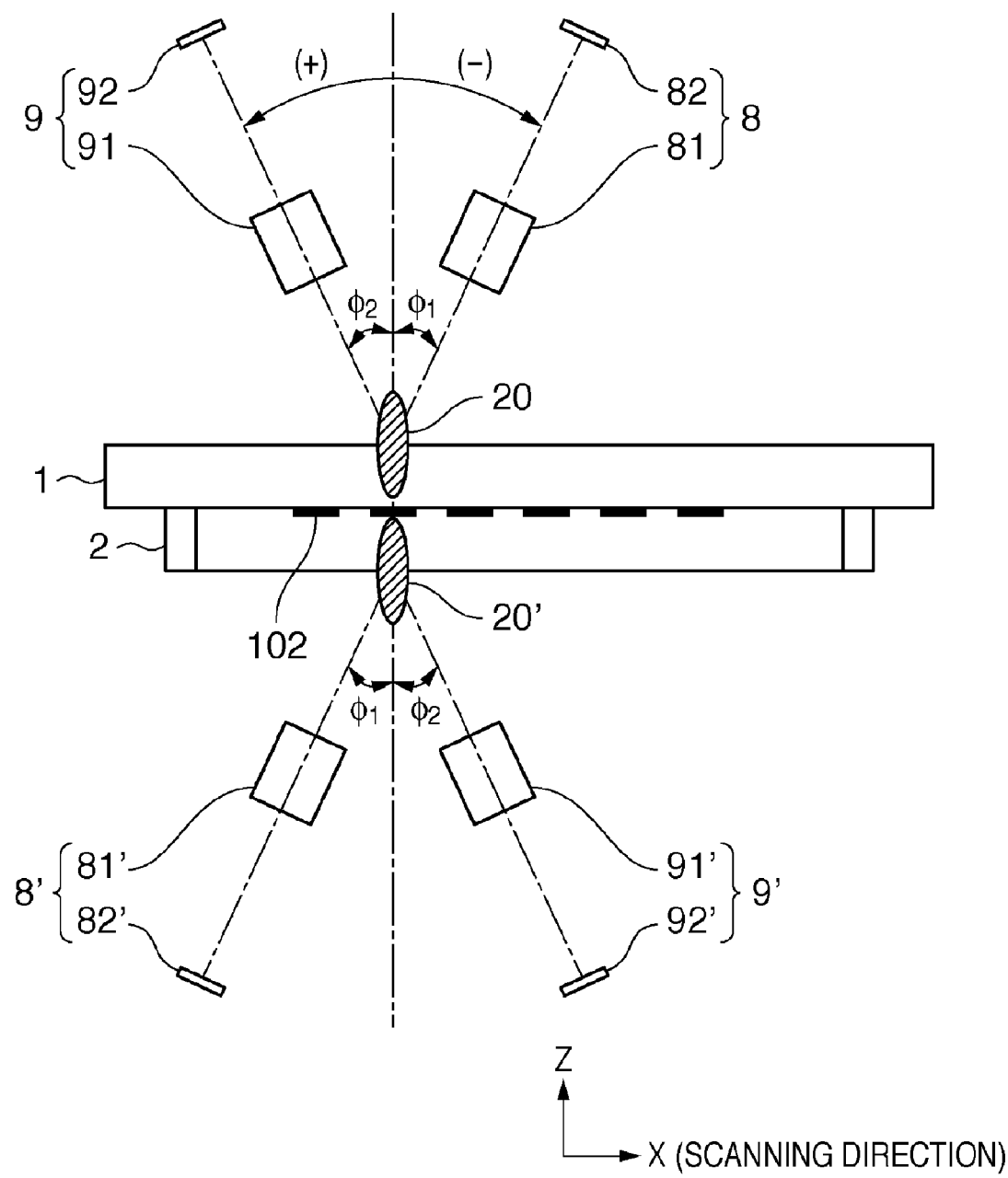
FIG. 2 is a sectional view showing the foreign particle inspection apparatus according to the first embodiment.

FIG. 2 is a sectional view, which shows the basic arrangement of the entire photo-receiving units and the direction in which the polarization axis of a laser beam is set, when viewed from the direction in which a laser beam is projected to the reticle, i.e., from the Y direction. The optical axis of light received by photo-receiving imaging lenses 81 and 82, i.e., the optical axis of the photo-receiving unit 8 is tilted by a first angle φ1 with respect to a plane including the optical axis of the light projecting unit 4 and the normal axis to the surface (the blank surface or the pellicle surface) of the object to be inspected. On the other hand, the optical axis of photo-receiving imaging lenses 91 and 92 (the optical axis of the photo-receiving unit 9) is tilted by another first angle φ2 with respect to a plane including the optical axis of the light projecting unit 4 and the normal axis to the surface (the blank surface or the pellicle surface) of the object to be inspected. The first angles φ1 and φ2 of the photo-receiving units 8 and 9, respectively, are different from each other.

A method of optimally setting the azimuth of the polarization axis of a projected laser beam will be described subsequently. FIG. 3 shows the relationship between the azimuth of the polarization axis and the output of the intensity of scattered light for each particle size (10 μm, 15 μm, and 30 μm). FIG. 3 shows the relationship between the azimuth of the polarization axis and the output from the photo-receiving unit 8 for φ1=−30°. The azimuth of the polarization axis of projected light can be changed by rotating the λ/2 plate 43 included in the light projecting unit 4. Let α be a second angle serving as the angle of the polarization axis of projected light with respect to a plane including the optical axis of the light projecting unit 4 and the normal axis to the surface of the object to be inspected. Referring to FIGS. 2 and 3, the counterclockwise direction is the positive directions of the angles φ and α. For example, φ1<0 and φ2>0 in FIG. 2.

The foreign particle inspection apparatus needs to uniquely determine the particle size based on the outputs from the photo-receiving units 8 and 9. Under the above-mentioned inspection conditions, the output of a signal from light scattered by a particle rises in the particle size order of 10 μm<15 μm<30 μm when the azimuth α of the polarization axis is −90° to +30°. Note that upon detection while the photo-receiving unit 9 satisfies φ2=+30°, the output of a signal from light scattered by a particle rises in the particle size order of 10 μm<15 μm<30 μm when the azimuth α of the polarization axis is +90° to −30°.

FIG. 4 shows the relationship between the output of the intensity of light diffracted by the pattern and that of light scattered by a 10-μm particle with respect to the azimuth of the polarization axis. As can be understood from FIG. 4, to set the output of light diffracted by the pattern to be smaller than that of light scattered by a 10-μm particle while the photo-receiving unit 8 satisfies φ1=−30°, it is necessary to set the azimuth α of the polarization axis to be equal to or more than −40°. Note that in detection while the photo-receiving unit 9 satisfies φ2=+30°, it is necessary to set the azimuth α of the polarization axis to be equal to or smaller than +40°. Under the above-mentioned conditions of the azimuth of the polarization axis, the qualitative relationship between the output of light diffracted by the pattern and that of light scattered by a 10-μm particle remains the same irrespective of the type of pattern.

In the above-mentioned embodiment, the apparatus is set such that the discrimination performance between a signal from light scattered by a particle on the surface of the object to be inspected and that of light diffracted by the pattern improves, and that the intensity of scattered light increases in proportion to increases in the particle size. To attain this state, the λ/2 plate 43 sets the azimuth α of the polarization axis within the range of ±30° with respect to a plane including the optical axis of the light projecting unit 4 and the normal axis to the surface of the object to be inspected. The azimuth α of the polarization axis on the side of the pellicle surface can be optimized in the same way.

A method of optimally setting the azimuths of the optical axes of the photo-receiving units 8 and 9 will be described. The first angles φ1 and φ2 of the optical axes of the photo-receiving units 8 and 9 are desirably set from 25° (inclusive) to 90° (exclusive) in order to avoid falsely detecting light diffracted by the pattern as scattered light. In addition, differences (φ−α) between the first angles φ of the optical axes of the photo-receiving units 8 and 9 and the second angle serving as the azimuth of the polarization axis need to be set within the range of −60° (inclusive) to +60° (inclusive). This is because as the optical axes of the photo-receiving units 8 and 9 are tilted while the azimuth of the polarization axis is fixed, a condition in which the intensity of scattered light increases in proportion to increases in the particle size does not hold.

For example, as shown in FIG. 5A, an azimuth α which satisfies a condition in which the intensity of scattered light increases in proportion to increases in the particle size is −90°≦α≦+30° for φ1=−30°, as mentioned above (FIG. 5A). However, when the angle φ1 is increased to φ1' by Δφ1=−10° for α=+30° (φ'=−40°), the azimuth α which satisfies that condition shifts to −100°≦α'≦+20° (FIG. 5B). At this time, α=+30°>α'=+20°, so the output of a signal from scattered light does not rise in the particle size order of 10 μm<15 μm<30 μm (FIG. 5C).

It is therefore necessary that the optical axes of the photo-receiving units are tilted by an angle from 25° (inclusive) to 90° (exclusive) with respect to a plane including the optical axis of the light projecting unit and the normal axis to the surface of the object to be inspected, and are tilted by an angle within the range of ±60° with respect to the polarization direction of linearly polarized light.

[Second Embodiment]

A method of discriminating between a signal from light scattered by a particle on the surface of an object to be inspected and that of light diffracted by the pattern by a controller in a foreign particle inspection apparatus will be described.

Figure 6:
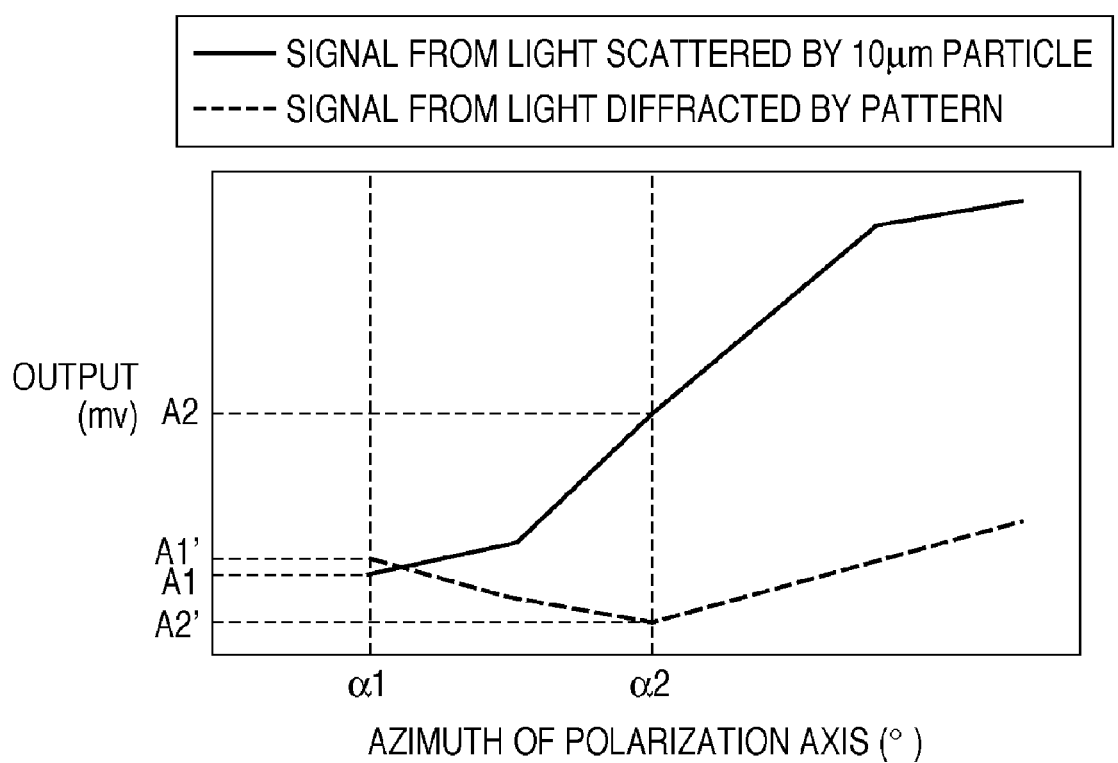
FIG. 6 is a graph showing the relationship between the azimuth of the polarization axis, and the output of light scattered by a particle and that of light diffracted by the pattern.

The output curve of light scattered by a 10-μm particle on the surface of an object to be inspected and that of light diffracted by the pattern with respect to an azimuth α of the polarization axis differ from each other, as shown in FIG. 6. By paying attention to this fact, the azimuth α of the polarization axis is changed upon detecting a signal during inspection, and detection is performed again. Based on the differences between the plurality of outputs obtained by the series of detection operations, the controller determines whether the output bears the information of a foreign particle present on the surface of the object to be inspected or a factor, other than the foreign particle, such as light diffracted by the pattern. The controller also performs this determination based on the ratios between the plurality of outputs before and after the azimuth α of the polarization axis is changed. For example, assume that the output has changed from A1 or A1' to A2 or A2' upon switching the azimuth α of the polarization axis from α1 to α2. As shown in FIG. 6, A2-A1>0 if the output bears the information of light scattered by a particle, and A2'-A1'<0 if the output bears the information of light diffracted by the pattern. From this fact, it is possible to discriminate between light scattered by a particle and that diffracted by the pattern. This discrimination can also be done from the fact that A2/A1>1 if the output bears the information of light scattered by a particle, and A2'/A1'<1 if the output bears the information of light diffracted by the pattern.

The reference value of the output of a signal from a reference particle (e.g., a 10-μm particle) for each azimuth of the polarization axis is acquired (recorded) in advance. From the relationship of the detection signal output with respect to the acquired output, it is determined whether the output bears the information of light scattered by a particle or that diffracted by the pattern. For example, outputs A1 and A2 when the output of a 10-μm particle on the surface of the object to be inspected has changed from A1 to A2 upon switching the azimuth of the polarization axis from α1 to α2 are recorded. Assume that the output has changed from A1' to A2' upon changing the azimuth of the polarization axis from α1 to α2 during actual inspection. At this time, if A1-A1'<A2-A2', the output is determined to bear the information of light diffracted by the pattern.

[Third Embodiment]

FIG. 7 shows the inspection result obtained in a first state defined by φ=−30° and α=0° using a graph in which the abscissa indicates the particle size and the ordinate indicates the output of light scattered by a particle. According to this result, as the particle size exceeds A μm, a relationship in which the intensity of scattered light increases in proportion to increases in the particle size does not hold. At the same time, when the inspection is performed in a second state defined by φ=−30° and α=+60°, as shown in FIG. 8, a relationship in which the intensity of scattered light increases in proportion to increases in the particle size holds even when the particle size exceeds A μm. Note that this relationship does not hold when the particle size is smaller than A μm. By taking account of these facts, the polarization state of projected light may be switched appropriately in accordance with the particle size to be discriminated. More specifically, when one photo-receiving unit is used, the entire surface of the object to be inspected is inspected by relatively scanning a light projecting unit 4 and a photo-receiving unit 8 along the surface of the object to be inspected a plurality of times by changing the azimuth of the polarization axis of projected light while maintaining the positional relationship between the light projecting unit 4 and the photo-receiving unit 8. In the interval between successive scanning operations, the azimuth of the polarization axis of projected light is switched between α=0° when the particle size to be discriminated is equal to or smaller than A μm, and a condition in which the polarization axis is perpendicular to the optical axis of the photo-receiving unit 8 when the particle size is equal to or larger than A μm.

The angles φ in the first and second states shown in FIGS. 7 and 8, respectively, have the same value of −30°, whereas the azimuths α in these states have different values of 0° and +60°. That is, the difference (φ−α) between the first and second angles differs between the first and second states.

Figure 9:
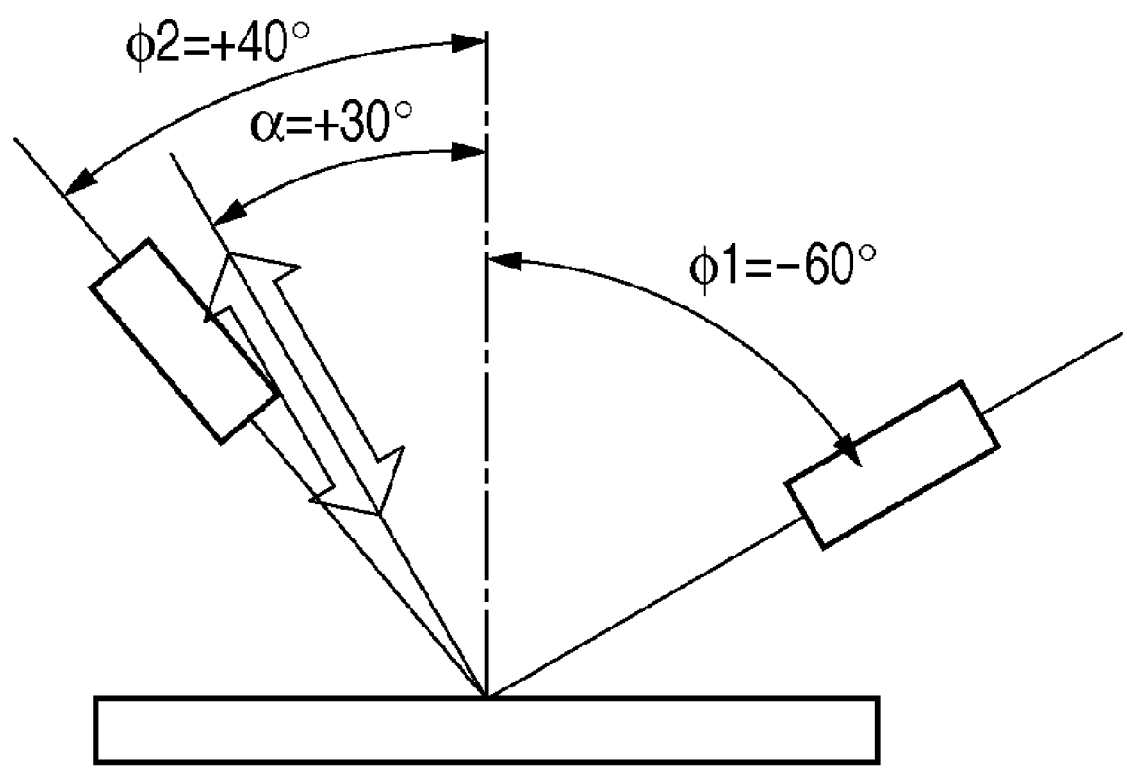
FIG. 9 is a diagram showing the relationship between the azimuth of the polarization axis and that of optical axes of two photo-receiving units for $\phi 1 = -60°$, $\phi 2 = +40°$, and $\alpha = +30°$.

When a plurality of photo-receiving units are provided, the entire surface of the object to be inspected is inspected by relatively scanning the light projecting unit 4 and a plurality of photo-receiving units 8 and 9 along the surface of the object to be inspected once while maintaining the positional relationship between the light projecting unit 4 and the photo-receiving units 8 and 9. In this case, for example, φ1=−60°, α=+30°, and φ2=+40° are set (FIG. 9). This makes it possible to satisfy a condition in which the output of the intensity of scattered light increases in proportion to increases in the particle size for the particle size to be discriminated without detecting any light diffracted by the pattern, as mentioned above, in the photo-receiving units 8 and 9, and to quickly perform inspection.

Figure 11A:
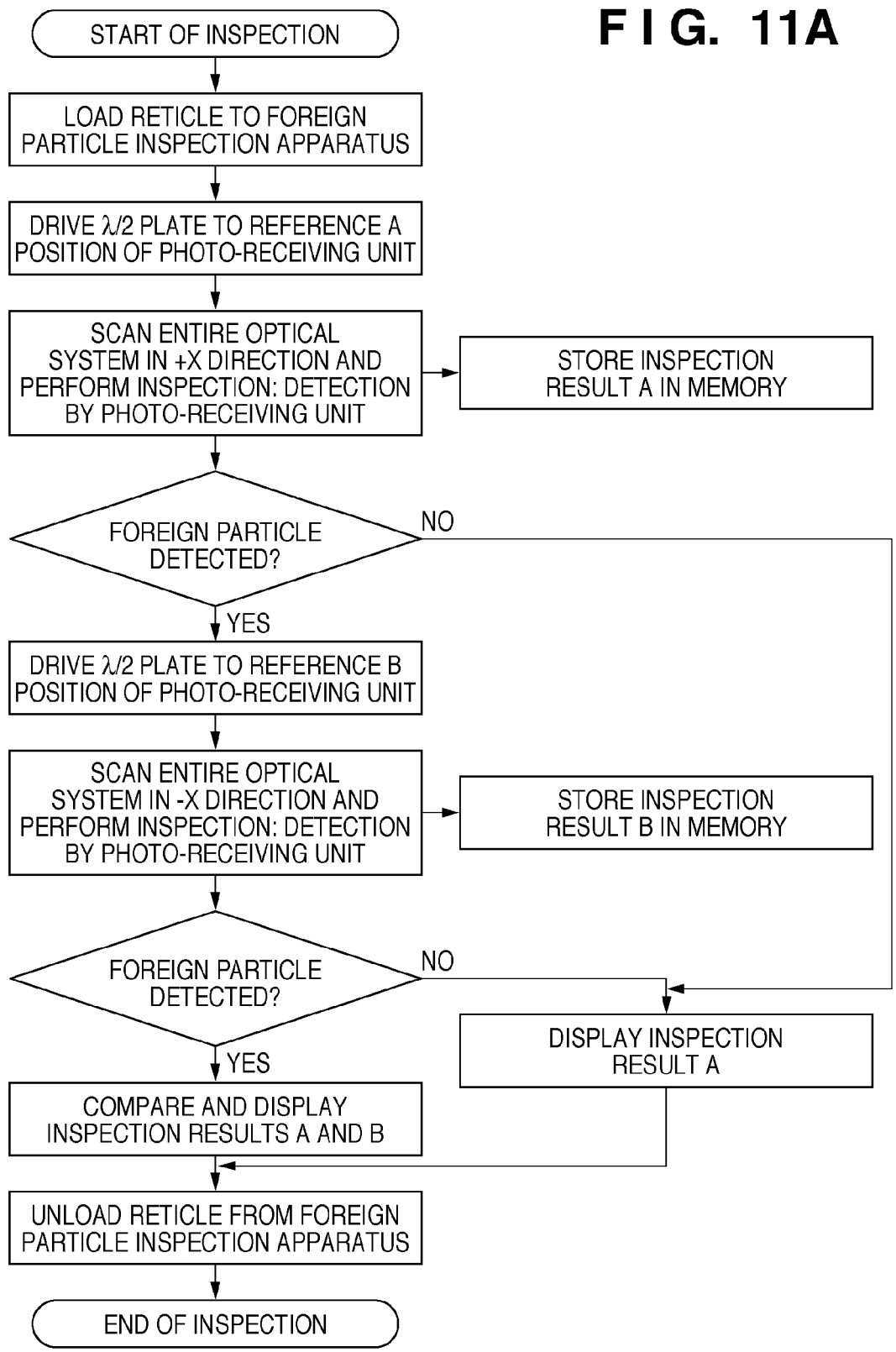
FIG. 11A is a flowchart illustrating an example of an inspection sequence.

FIG. 11A is a flowchart illustrating a sequence of inspection using one photo-receiving unit 8 by reciprocating an entire optical system 10. First, inspection is performed by scanning the photo-receiving unit 8 in the +X direction while the azimuth α is in the first state (reference A position). If no foreign particle is detected, the inspection ends. If a foreign particle is detected, inspection is performed again by setting the azimuth α to the second state (reference B position) and scanning the photo-receiving unit 8 in the −X direction. Accordingly, if a foreign particle is detected in this flowchart, the entire optical system 10 is scanned a plurality of times. To change the scanning direction of the entire optical system 10, it is necessary to rotate a λ/2 plate 43. The outputs from the photo-receiving unit 8 upon the scanning operations in the +X and −X directions are stored in advance in the inspection apparatus as the detected particle sizes at respective coordinates per, for example, square millimeter. A smaller detected particle size of two inspection results obtained by the photo-receiving unit 8 at each coordinate is determined as a final inspection result. It is possible to precisely detect foreign particles because two outputs from the photo-receiving unit 8 bear the information of the same detected particle size when a foreign particle is detected.

Figure 11B:
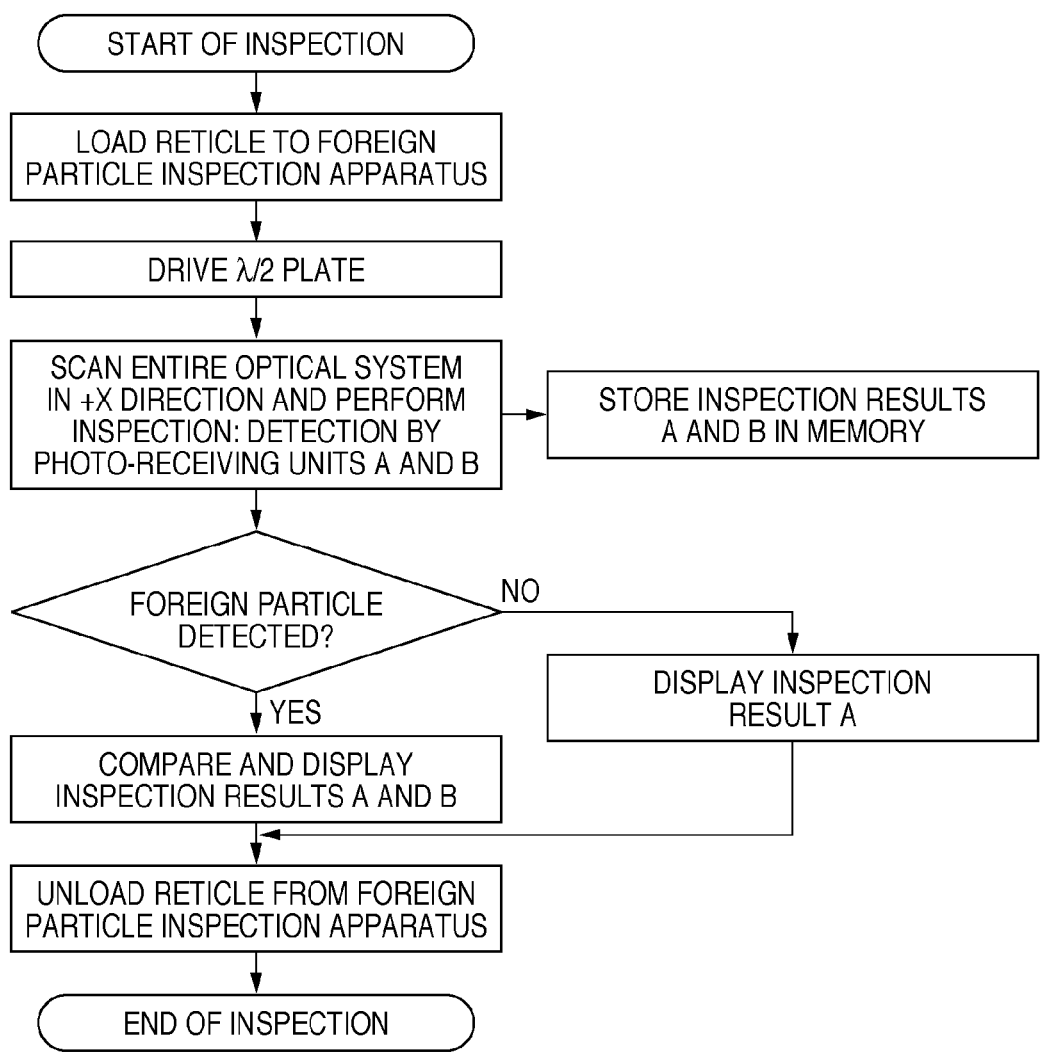
FIG. 11B is a flowchart illustrating another example of the inspection sequence.
Figure 12:
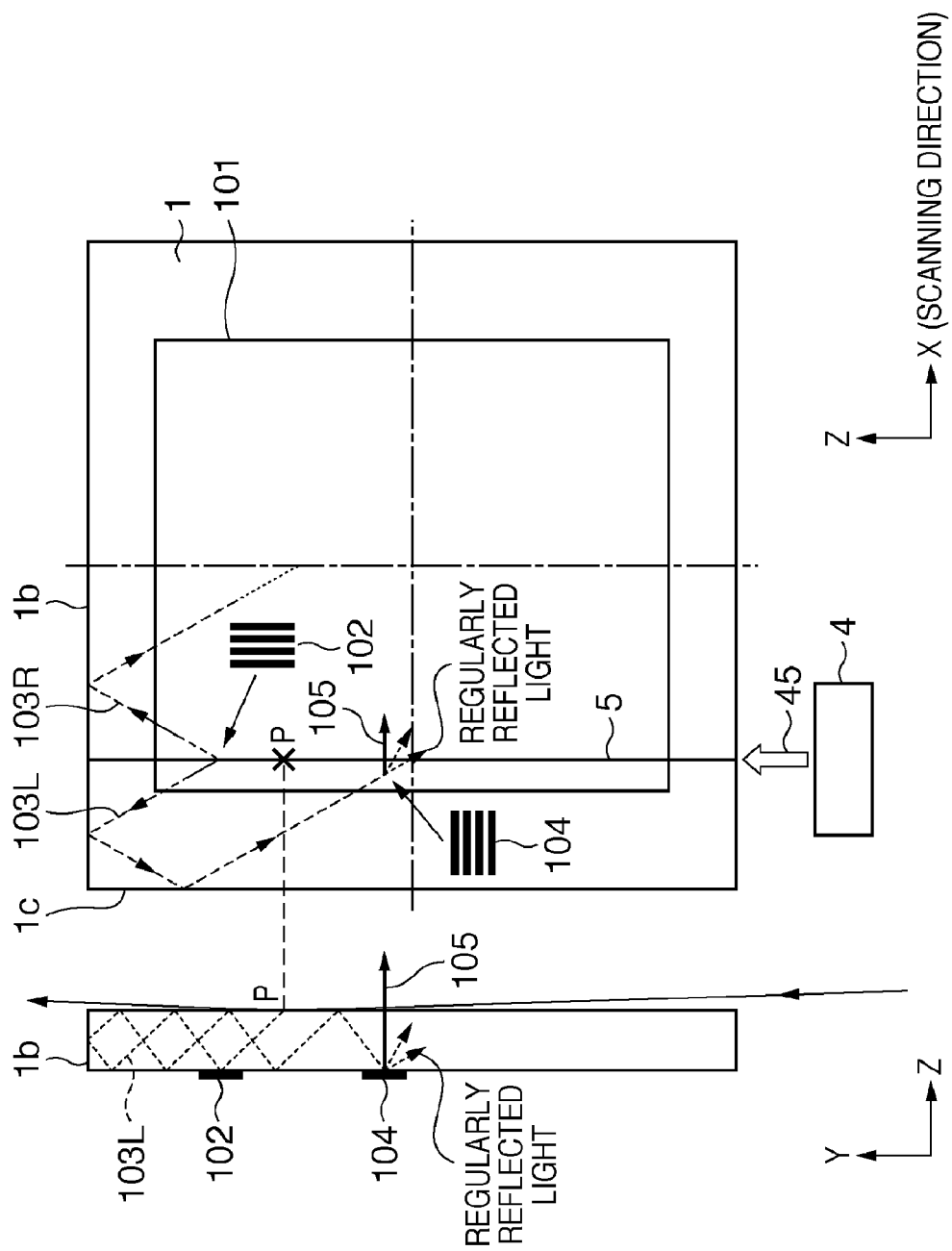
FIG. 12 is an explanatory view showing a mechanism of falsely detecting light diffracted by the pattern as scattered light.
Figure 13:
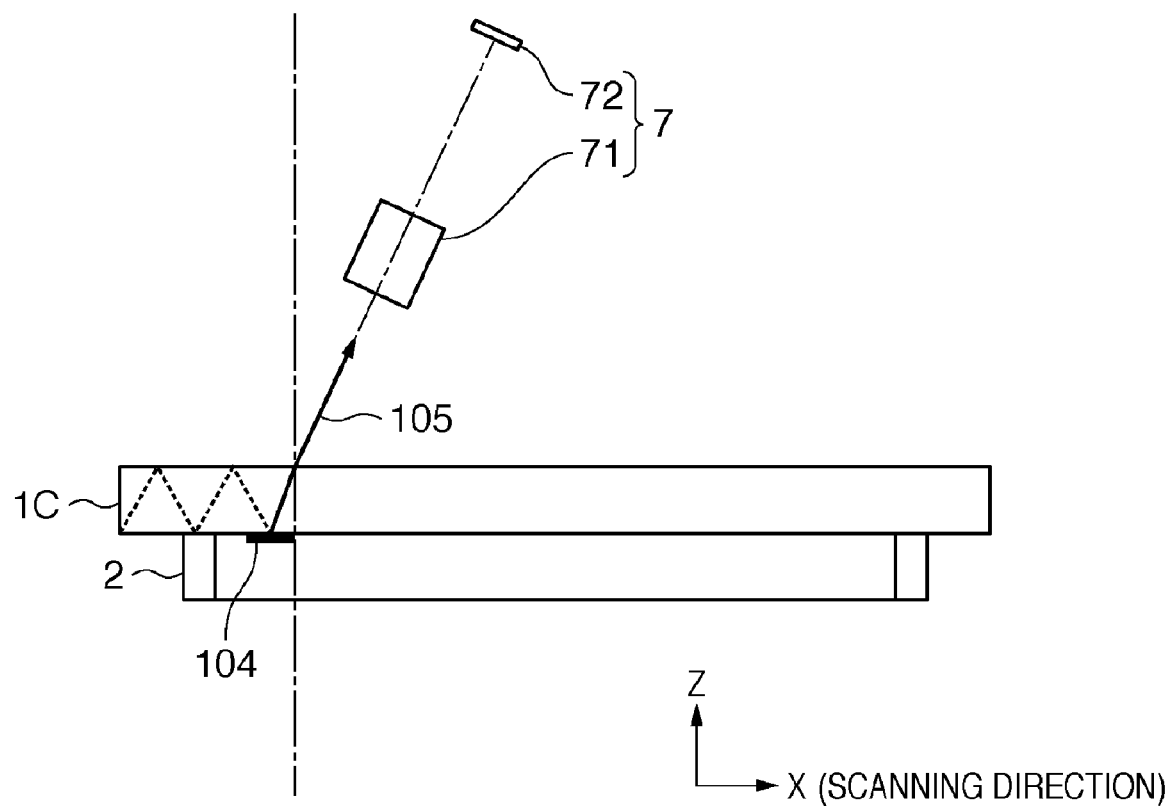
FIG. 13 is an explanatory view showing the mechanism of falsely detecting light diffracted by the pattern as scattered light.

FIG. 11B is a flowchart illustrating a sequence of inspection using two photo-receiving units 8 and 9. The λ/2 plate 43 sets the azimuth α of the polarization axis within the range of −40° (inclusive) to +40° (inclusive). Both the optical axes of the photo-receiving units 8 and 9 are tilted by an angle from 25° (inclusive) to 90° (exclusive) with respect to a plane including the optical axis of the light projecting unit and the normal axis to the surface of the object to be inspected, and are tilted by an angle within the range of ±60° with respect to the polarization direction of linearly polarized light. In this state, simultaneous inspection is performed by scanning the photo-receiving units 8 and 9 in the +X direction. This inspection method never causes false detection due to light diffracted by the pattern in the photo-receiving units 8 and 9. Moreover, adjusting both the photo-receiving units 8 and 9 to satisfy the above-mentioned inspection condition obviates the need to reciprocate the entire optical system 10 by rotating the λ/2 plate 43 (the rotational position of the λ/2 plate 43 is fixed). This makes it possible to quickly, precisely detect foreign particles.

FIG. 11C is a flowchart illustrating another sequence of inspection using two photo-receiving units 8 and 9. In the flowchart illustrated in FIG. 11C, inspection is performed by scanning the photo-receiving units 8 and 9 in the +X direction. If no foreign particle is detected, the inspection ends. If a foreign particle is detected, inspection is performed again by scanning the photo-receiving units 8 and 9 in the −X direction. The λ/2 plate 43 is rotated to change the scanning direction. As a final result, the size of the foreign particle, light scattered by a foreign particle, and light diffracted by the pattern are determined in accordance with changes in the output (the differences between the outputs, the ratios between the outputs, and changes in the ratios of the outputs to those of a reference particle) from each of the photo-receiving units 8 and 9 in each scanning direction.

Assume that one photo-receiving unit 8 is used. When the entire optical system 10 is scanned in the +X direction and inspection is performed, the λ/2 plate is rotated to set the polarization axis of projected light in a direction perpendicular to the optical axis of the photo-receiving unit (inspection for a large-size foreign particle). When the entire optical system 10 is scanned in the −X direction, the λ/2 plate is rotated to set the polarization axis at an azimuth at which the angle α of the polarization axis of projected light falls within the range of ±40°, and which falls within the range of ±60° with respect to the optical axis of the photo-receiving unit (inspection for a small-size foreign particle). That is, the rotational position of the λ/2 plate is set in accordance with the foreign particle size to be discriminated for each scanning.

Assume that two light-receiving units are used. When the entire optical system 10 is scanned in the +X direction and inspection is performed, the λ/2 plate is rotated. The polarization axis is fixed at an azimuth which falls within the range of ±40° with respect to a plane that is perpendicular to the optical axis of at least one photo-receiving unit and includes the optical axis of the light projecting unit and the normal axis to the surface of the object to be inspected, and which falls within the range of ±60° with respect to the optical axis of the other photo-receiving unit. That is, the rotational position of the λ/2 plate is fixed so that the two photo-receiving units can perform simultaneous inspection for different foreign particle sizes to be discriminated.

The present invention is applicable not only to a semiconductor exposure apparatus used in manufacturing, e.g., a semiconductor device and a liquid-crystal display device, but also to various high-precision processing apparatuses and various high-presition measuring apparatuses, and is effective in detecting a foreign particle on the surface to be inspected of an object to be processed or measured.

[Explanation of Exposure Apparatus]

Figure 14:
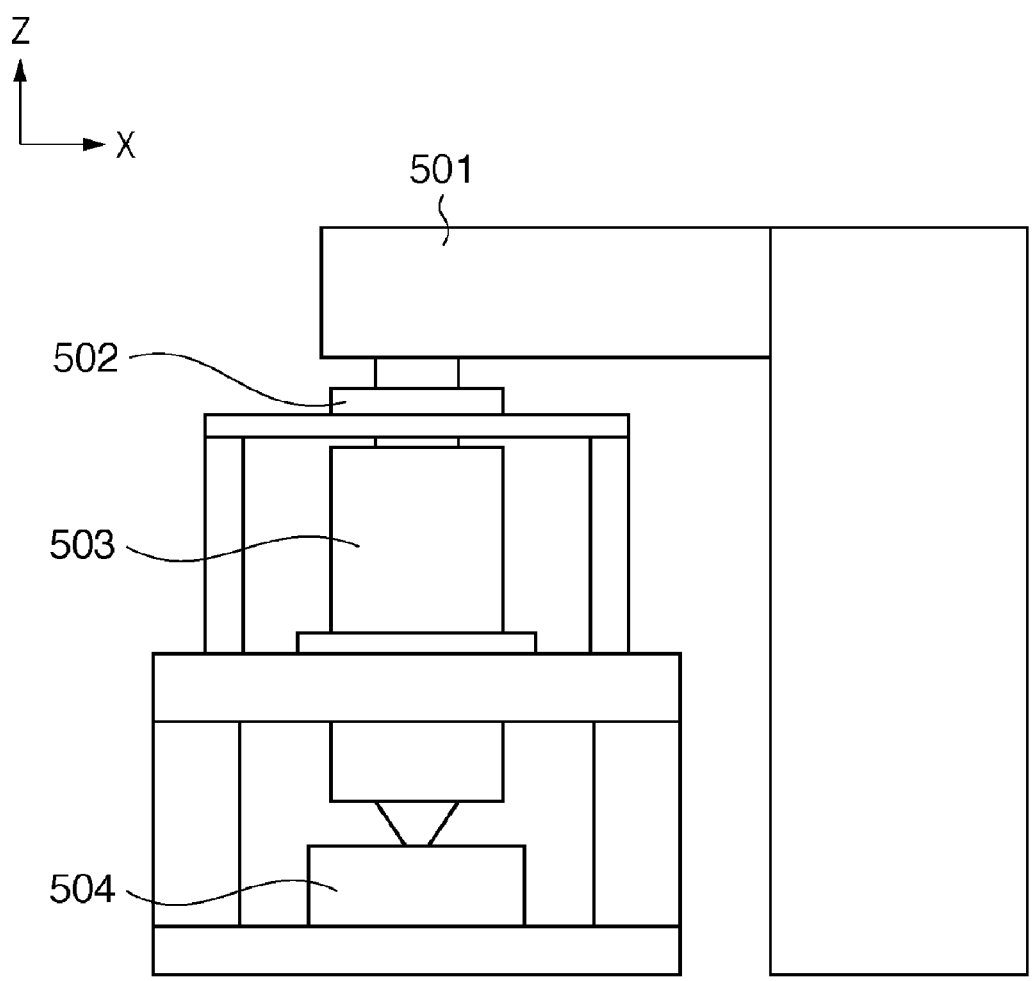
FIG. 14 is a view showing an example of an exposure apparatus.

An exemplary exposure apparatus which transfers the pattern of a reticle onto a substrate to expose the substrate and to which the present invention is applied will be explained. The exposure apparatus includes an illumination apparatus 501, a reticle stage 502 which mounts a reticle, a projection optical system 503, and a substrate stage 504 which holds a substrate, as shown in FIG. 14. As mentioned above, a driving mechanism (not shown) scans the substrate stage 504 in the Y direction, and moves it in the X direction step by step. The exposure apparatus performs scanning exposure by projecting a circuit pattern formed on a reticle onto a substrate.

The illumination apparatus 501 illuminates a reticle on which a circuit pattern is formed, and includes a light source unit and illumination optical system. The light source unit uses, for example, a laser as the light source. The laser can be, e.g., an ArF excimer laser having a wavelength of about 193 nm, a KrF excimer laser having a wavelength of about 248 nm, or an F2 excimer laser having a wavelength of about 153 nm. However, the type of laser is not particularly limited to an excimer laser and may be, for example, a YAG laser, and the number of lasers is also not particularly limited. When a laser is used as the light source, an optical system for shaping a collimated light beam from the laser beam source into a desired beam shape, and an optical system for converting a coherent laser beam into an incoherent laser beam are preferably used. Also, the light source which can be used for the light source unit is not particularly limited to a laser, and one or a plurality of mercury lamps or xenon lamps can be used. The illumination optical system illuminates a mask and includes, e.g., a lens, mirror, light integrator, and stop.

The projection optical system 503 can be, e.g., an optical system including a plurality of lens elements alone, an optical system including a plurality of lens elements and at least one concave mirror, an optical system including a plurality of lens elements and at least one diffractive optical element such as a kinoform, or an optical system including only mirrors.

The reticle stage 502 and wafer stage 504 can move by, for example, a linear motor. The stages 502 and 504 move synchronously. Actuators (driving mechanisms; not shown) are provided to the wafer stage 504 and the reticle stage 502 to align the reticle pattern onto the wafer.

An embodiment of a method of manufacturing a device using the above-mentioned exposure apparatus will be explained next.

Devices (e.g., a semiconductor integrated circuit device and a liquid crystal display device) are manufactured by a step of exposing a substrate to radiant energy using the exposure apparatus according to the above-mentioned embodiment, a step of developing the substrate exposed in the exposing step, and other known steps (e.g., etching, resist removing, dicing, bonding, and packaging steps) of processing the substrate developed in the developing step.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-108291, filed Apr. 17, 2008, which is hereby incorporated by reference herein in its entirety.

What is claimed is:

1. A foreign particle inspection apparatus including a light projecting unit which projects light to a surface of an object to be inspected, a photo-receiving unit which receives the light that is projected to the surface by the light projecting unit and scattered by the surface, and a controller which determines a size of a foreign particle on the surface based on the output from the photo-receiving unit, wherein the light projecting unit is arranged such that an optical axis of the light projecting unit is tilted with respect to the surface, the photo-receiving unit is arranged such that an optical axis of the photo-receiving unit is tilted by a first angle with respect to a plane including the optical axis of the light projecting unit and a normal axis to the surface, and when an angle of a polarization axis of the projected light with respect to the plane is defined as a second angle, the controller controls at least one of the polarization axis of the projected light and the arrangement of the photo-receiving unit so that differences between the first angle and the second angle become a first state and a second state which are different from each other, and wherein the controller determines the size of the foreign particle based on the output from the photo-receiving unit in the first state and the output from the photo-receiving unit in the second state using a data which represents a relation between the size of a foreign particle and the output from the photo-receiving unit when the photo-receiving unit receives the light from the foreign particle, and wherein the data which represents the relation between the size of a foreign particle and an output from the photo-receiving unit when the photo-receiving unit receives the light from the foreign particle includes a data where the relation between the size of the foreign particle and the output from the photo-receiving unit when the photo-receiving unit receives the light from the foreign particle is linear, when the difference between the first angle and the second angle is in the second state, in a range of the size of the foreign particle where the relation between the size of the foreign particle and the output from the photo-receiving unit when the photo-receiving unit receives the light from the foreign particle is not linear when the difference between the first angle and the second angle is in the first state.

2. The apparatus according to claim 1, wherein the differences between the first angle and the second angle in both the first state and the second state fall within a range of −60° (inclusive) to +60° (inclusive).

3. The apparatus according to claim 1, wherein the difference between the first angle and the second angle in one of the first state and the second state is 90°.

4. The apparatus according to claim 1, wherein the second angle falls within a range of −40° (inclusive) to +40° (inclusive).

5. The apparatus according to claim 1, wherein the controller relatively moves the light projecting unit and the photo-receiving unit along the surface of the object to be inspected a plurality of times while maintaining a positional relationship between the light projecting unit and the photo-receiving unit, and controls the polarization axis of the projected light so that the second angle changes for each of the plurality of moving operations, thereby setting the first state and the second state.

6. The apparatus according to claim 1, wherein
the photo-receiving unit includes a plurality of photo-receiving units, and
the controller relatively moves the light projecting unit and the plurality of light receiving units along the surface of the object to be inspected while maintaining a positional relationship between the light projecting unit and the plurality of photo-receiving units, thereby obtaining the plurality of outputs from the plurality of photo-receiving units.

7. The apparatus according to claim 6, wherein the controller determines based on the plurality of outputs whether the plurality of outputs bear information of a foreign particle present on the surface of the object to be inspected or a factor other than the foreign particle.

8. The apparatus according to claim 7, wherein the controller determines whether the plurality of outputs bear information of the foreign particle or the factor other than the foreign particle based on one of differences between the plurality of outputs, ratios between the plurality of outputs, and a difference between one of the plurality of outputs and a reference value of the output.

9. The apparatus according to claim 1, wherein the size of a foreign particle to be inspected when the difference between the first angle and the second angle is in the first state is smaller than the size of the foreign particle to be inspected when the difference between the first angle and the second angle is in the second state.

10. An exposure apparatus which transfers a pattern of a reticle onto a substrate to expose the substrate, the apparatus comprising:
a foreign particle inspection apparatus configured to inspect a surface of the reticle for a foreign particle,
wherein said foreign particle inspection apparatus includes
a light projecting unit configured to project light to a surface of an object to be inspected,
a photo-receiving unit configured to receive the light which is projected to the surface by said light projecting unit and scattered by the surface, and
a controller configured to determine a size of a foreign particle on the surface based on the output from said photo-receiving unit,
said light projecting unit is arranged such that an optical axis of said light projecting unit is tilted with respect to the surface,
said photo-receiving unit is arranged such that an optical axis of said photo-receiving unit is tilted by a first angle with respect to a plane including the optical axis of said light projecting unit and a normal axis to the surface, and
when an angle of a polarization axis of the projected light with respect to the plane is defined as a second angle, said controller controls at least one of the polarization axis of the projected light and the arrangement of said photo-receiving unit so that differences between the first angle and the second angle become a first state and a second state which are different from each other, and
wherein the controller determines the size of the foreign particle based on the output from the photo-receiving unit in the first state and the output from the photo-receiving unit in the second state using a data which represents a relation between the size of the foreign particle and the output from the photo-receiving unit when the photo-receiving unit receives the light from the foreign particle, and
wherein the data which represents the relation between the size of a foreign particle and an output from the photo-receiving unit when the photo-receiving unit receives the light from the foreign particle includes a data where the relation between the size of the foreign particle and the output from the photo-receiving unit when the photo-receiving unit receives the light from the foreign particle is linear, when the difference between the first angle and the second angle is in the second state, in a range of the size of the foreign particle where the relation between the size of the foreign particle and the output from the photo-receiving unit when the photo-receiving unit receives the light from the foreign particle is not linear when the difference between the first angle and the second angle is in the first state.

11. A method of manufacturing a device, the method comprising:
exposing a substrate to radiant energy using an exposure apparatus;
developing the exposed substrate; and
processing the developed substrate to manufacture the device,
wherein the exposure apparatus includes a foreign particle inspection apparatus configured to inspect a surface of the reticle for a foreign particle,
the foreign particle inspection apparatus includes
a light projecting unit configured to project light to a surface of an object to be inspected,
a photo-receiving unit configured to receive the light which is projected to the surface by the light projecting unit and scattered by the surface, and a controller configured to determine a size of a foreign particle on the surface based on the output from the photo-receiving unit, the light projecting unit is arranged such that an optical axis of the light projecting unit is tilted with respect to the surface, the photo-receiving unit is arranged such that an optical axis of the photo-receiving unit is tilted by a first angle with respect to a plane including the optical axis of the light projecting unit and a normal axis to the surface, and when an angle of a polarization axis of the projected light with respect to the plane is defined as a second angle, the controller controls at least one of the polarization axis of the projected light and the arrangement of the photo-receiving unit so that differences between the first angle and the second angle become a first state and a second state which are different from each other, and wherein the controller determines the size of the foreign particle based on the output from the photo-receiving unit in the first state and the output from the photo-receiving unit in the second state using a data which represents a relation between the size of the foreign particle and the output from the photo-receiving unit when the photo-receiving unit receives the light from the foreign particle, and wherein the data which represents the relation between the size of a foreign particle and an output from the photo-receiving unit when the photo-receiving unit receives the light from the foreign particle includes a data where the relation between the size of the foreign particle and the output from the photo-receiving unit when the photo-receiving unit receives the light from the foreign particle is linear, when the difference between the first angle and the second angle is in the second state, in a range of the size of the foreign particle where the relation between the size of the foreign particle and the output from the photo-receiving unit when the photo-receiving unit receives the light from the foreign particle is not linear when the difference between the first angle and the second angle is in the first state.

* * * * *